United States Patent
Adler et al.

(10) Patent No.: US 10,300,244 B2
(45) Date of Patent: May 28, 2019

(54) UNRAVELABLE CATHETER

(71) Applicant: RENALSENSE LTD., Jerusalem (IL)

(72) Inventors: Michael Adler, Kfar Vradim (IL); Mor Grinstein, Modi'in (IL); Jack Yehoshua Mantinband, Efrata (IL)

(73) Assignee: RENALSENSE LTD., Jerusalem (IL)

( * ) Notice: Subject to any disclaimer, the term of this patent is extended or adjusted under 35 U.S.C. 154(b) by 281 days.

(21) Appl. No.: 14/906,182

(22) PCT Filed: Jul. 17, 2014

(86) PCT No.: PCT/IL2014/050645
§ 371 (c)(1),
(2) Date: Jan. 19, 2016

(87) PCT Pub. No.: WO2015/011700
PCT Pub. Date: Jan. 29, 2015

(65) Prior Publication Data
US 2016/0184550 A1 Jun. 30, 2016

Related U.S. Application Data

(60) Provisional application No. 61/856,809, filed on Jul. 22, 2013.

(51) Int. Cl.
*A61M 25/00* (2006.01)
*A61M 25/01* (2006.01)
(Continued)

(52) U.S. Cl.
CPC .... *A61M 25/0023* (2013.01); *A61M 25/0009* (2013.01); *A61M 25/10* (2013.01);
(Continued)

(58) Field of Classification Search
CPC .......... A61M 25/0009; A61M 25/0023; A61M 25/10; A61M 2025/0025;
(Continued)

(56) References Cited

U.S. PATENT DOCUMENTS 3,752,162 A    8/1973  Newash
3,993,078 A *  11/1976 Bergentz ................ A61B 17/11
                                                    606/156
(Continued)

FOREIGN PATENT DOCUMENTS

CN    201303995 Y    9/2009
CN    201759704 U    3/2011
(Continued)

OTHER PUBLICATIONS

European Search Report Of corresponding Application No. EP 14 82 9672, dated Jan. 24, 2017.
(Continued)

*Primary Examiner* — Adam Marcetich
(74) *Attorney, Agent, or Firm* — Leason Ellis LLP

(57) ABSTRACT

The invention is a catheter, which is formed from flexible material and has two basic configurations: An initial configuration, in which the catheter is supplied to the surgeon for insertion into the lumen of a patient, resembles a tension coil spring and a final configuration, which is an essentially linear configuration that is much longer and has a considerably smaller outer diameter than when it is in its initial configuration. The catheter is adapted to undergo a transformation from the initial configuration to the final configuration as it is pulled from its proximal end in order to withdraw it from the lumen of the patient.

7 Claims, 3 Drawing Sheets

(51) Int. Cl.
*A61M 25/10* (2013.01)
*A61M 39/08* (2006.01)

(52) U.S. Cl.
CPC .............. *A61M 2025/0025* (2013.01); *A61M 2025/0056* (2013.01); *A61M 2025/0188* (2013.01); *A61M 2039/087* (2013.01)

(58) Field of Classification Search
CPC .. A61M 2025/0056; A61M 2025/0188; A61M 2039/087; B29C 53/12; B29C 53/58; B29C 63/08; B29C 63/10; B29C 63/105; B29C 63/32
See application file for complete search history.

(56) References Cited

U.S. PATENT DOCUMENTS

| | | | | |
|---|---|---|---|---|
| 4,682,702 A * | 7/1987 | Gach | .................... | B65D 47/103 215/235 |
| 4,706,671 A | 11/1987 | Weinrib | | |
| 5,514,176 A * | 5/1996 | Bosley, Jr. | ................ | A61F 2/88 606/156 |
| 5,591,292 A * | 1/1997 | Blomqvist | .............. | B29C 53/78 156/244.13 |
| 5,607,338 A * | 3/1997 | Landi | ....................... | A63H 3/44 132/201 |
| 5,716,410 A | 2/1998 | Wang et al. | | |
| 5,944,929 A * | 8/1999 | Vallauri | ............... | B29O 53/582 156/162 |
| 5,958,167 A * | 9/1999 | Van Driel | ......... | A61M 25/0009 156/173 |
| 6,019,779 A * | 2/2000 | Thorud | ..................... | A61F 2/88 606/198 |
| 2002/0077680 A1* | 6/2002 | Noda | ..................... | A61B 17/00 607/105 |
| 2003/0153875 A1* | 8/2003 | Ostfeld | ............. | A61M 25/0017 604/171 |
| 2003/0211258 A1* | 11/2003 | Sridharan | ............. | B29C 53/581 428/35.2 |
| 2004/0087886 A1* | 5/2004 | Gellman | ................... | A61F 2/88 604/8 |
| 2004/0238480 A1* | 12/2004 | Gzybowski | ........ | B65D 39/0005 215/364 |
| 2005/0003118 A1* | 1/2005 | Takala | ................. | B29D 24/005 428/34.1 |
| 2005/0059929 A1 | 3/2005 | Bolmsjo et al. | | |
| 2005/0131423 A1* | 6/2005 | Yachia | ..................... | A61F 2/88 606/108 |
| 2005/0267442 A1* | 12/2005 | Von Oepen | ....... | A61M 25/0021 604/509 |
| 2007/0027531 A1* | 2/2007 | DiMatteo | .................. | A61F 2/07 623/1.42 |
| 2008/0154206 A1* | 6/2008 | Guo | ................... | A61M 25/0009 604/164.05 |
| 2008/0172040 A1* | 7/2008 | Smith | ............... | A61M 25/0017 604/544 |
| 2009/0264770 A1 | 10/2009 | Liu et al. | | |
| 2010/0121312 A1* | 5/2010 | Gielenz | ............. | A61M 25/0009 604/524 |
| 2010/0228233 A1* | 9/2010 | Kahn | ................... | A61M 5/1411 604/537 |
| 2011/0067775 A1* | 3/2011 | Simonsohn | ........ | H02G 15/1833 138/106 |
| 2013/0178833 A1* | 7/2013 | Sacchetti | .......... | A61M 5/14228 604/516 |
| 2014/0262859 A1* | 9/2014 | Knapp | ................ | A61M 25/002 206/210 |
| 2014/0276599 A1* | 9/2014 | Cully | ................ | A61M 25/0045 604/507 |

FOREIGN PATENT DOCUMENTS

| | | |
|---|---|---|
| CN | 201823151 U | 5/2011 |
| CN | 102711897 A | 10/2012 |
| CN | 102921049 A | 2/2013 |
| CN | 102973986 A | 3/2013 |
| CN | 203001664 U | 6/2013 |
| EP | 0 275 230 A2 | 7/1988 |
| EP | 0275230 A2 | 7/1988 |

OTHER PUBLICATIONS

International Preliminary Report on Patentability and Written Opinion in corresponding PCT Application No. PCT/IL2014/050645, dated Jan. 26, 2016.
International Search Report in corresponding PCT Application No. PCT/IL2014/050645, dated Nov. 2, 2014.
Chinese Office Action in corresponding CN Application No. 201480040657.9, dated Nov. 14, 2018 (an English translation attached hereto).

* cited by examiner

UNRAVELABLE CATHETER

CROSS-REFERENCE TO RELATED PATENT APPLICATIONS

This application is a U.S. National Phase Application under 35 U.S.C. §371 of International Patent Application No. PCT/IL2014/050645, filed Jul. 17, 2014, and claims the benefit of priority under 35 U.S.C. Section 119(e) of U.S. application Ser. No. 61/856,809, filed Jul. 22, 2013, all of which are incorporated by reference in their entireties. The International Application was published on Jan. 29, 2015 as International Publication No. WO 2015/011700 A1.

FIELD OF THE INVENTION

The present invention relates to the field of medical devices. More particularly, the present invention relates to catheters.

BACKGROUND OF THE INVENTION

Catheters are thin tubes which are widely used in medicine for a wide range of procedures. Catheters can be inserted in the body (body cavity, duct, or vessel) to treat diseases or perform surgical procedures (e.g. drainage, administration of fluids, or insertion of stents) in urological, gastrointestinal, neurovascular, ophthalmic, cardiovascular and other applications.

Insertion of a catheter is typically carried out by coating the catheter with a medical lubricating gel allowing it to be quickly and smoothly inserted with minimal pain to the patient. Since the diameter of the catheter is normally only marginally smaller than that of the lumen into which it is inserted, friction between the wall of the catheter and the tissue of the lumen frequently causes pain to the patient when the catheter is removed, even after a short period of time. For example, removal of a catheter that has been introduced into the bladder of a patient through the urethra is generally very painful to the patient. Another cause of pain to the patient is the growth of bacteria between the outer wall of the catheter and the wall of the body lumen. This bacteria forms a mucous that has adhesive properties, so that the catheter "sticks" to the wall of the body lumen, as though glued. On removal, this can cause great pain and trauma to the patient, including tearing of the lumen and bleeding.

It is therefore a purpose of the present invention to provide a catheter which after insertion, is easily removed from the body of a patient.

It is a further purpose of the present invention to provide a catheter which reduces the pain and trauma to the patient caused by the removal of the catheter.

Further purposes and advantages of this invention will appear as the description proceeds.

SUMMARY OF THE INVENTION

The invention is an unravelable catheter, which is formed from flexible material. The unravelable catheter has two basic configurations: an initial configuration, which has a shape resembling a tension coil spring, and a final configuration, which is essentially linear. The unravelable catheter is adapted to undergo a transformation from the initial configuration to the final configuration as the catheter is pulled out of a body lumen from its proximal end.

Embodiments of the unravelable catheter of the invention are manufactured by winding a long narrow piece of biocompatible polymer around a mandrel.

Embodiments of the unravelable catheter of the invention are manufactured by molding a biocompatible polymer into the shape of a tube having a wall comprised of two parallel spirals, one having relatively thick and the other having relatively thin wall thickness.

Embodiments of the catheter of the invention comprise at least one of the following: at least one balloon and a separate lumen for inflating it, an integral temperature sensor, a coating of antibacterial gel on its outer surface, a silver or copper wire looped around part or its entire outer surface.

Embodiments of the unravelable catheter of the invention comprising at least one safety feature to prevent accidental unraveling of the catheter.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

The invention is an unravelable catheter, which is formed from flexible material and has two basic configurations: An initial configuration, in which the catheter is supplied to the surgeon for insertion into the lumen of a patient, resembles a tension coil spring and a final configuration, which is an essentially linear configuration that is much longer and has a considerably smaller outer diameter than when it is in its initial configuration. The catheter is adapted to undergo a transformation from the initial configuration to the final configuration as it is pulled from its proximal end in order to withdraw it from the lumen of the patient.

Figure 1:
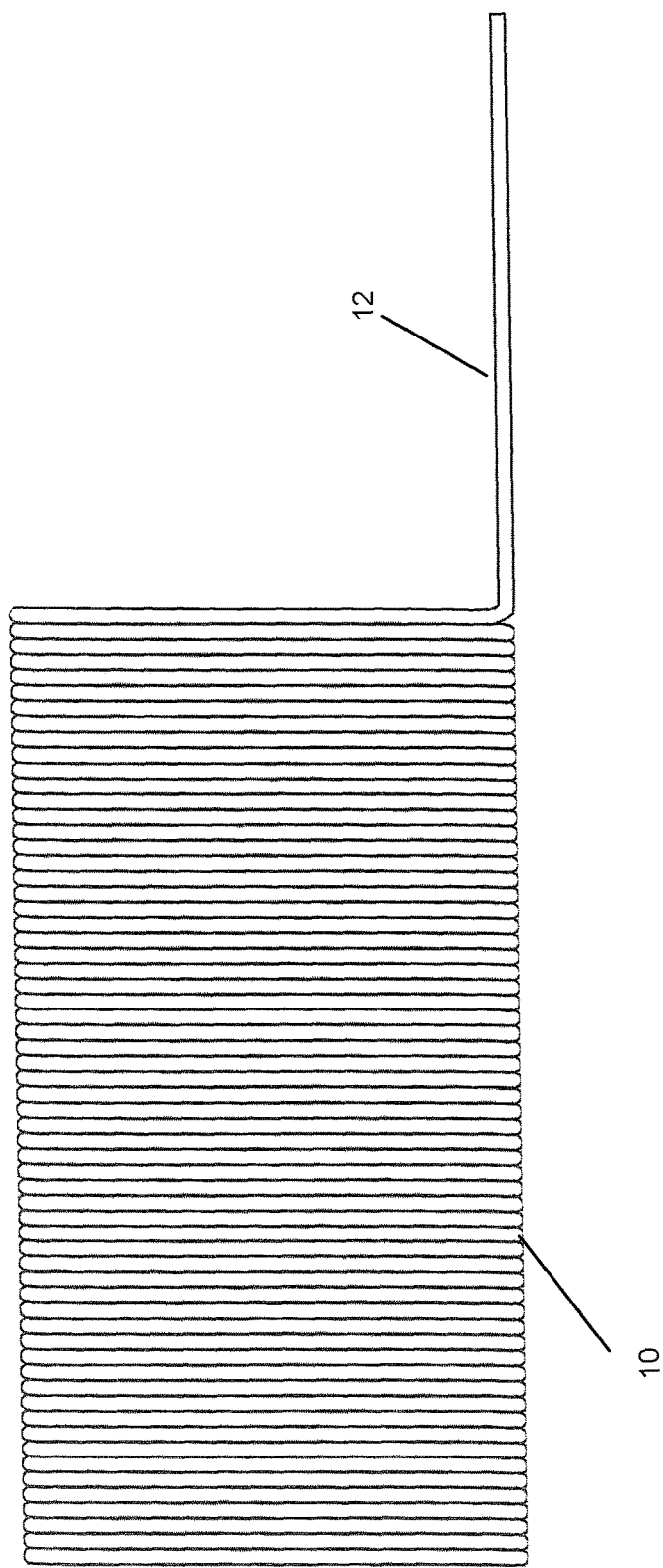
FIG. 1 schematically shows a catheter of the invention in its initial coiled configuration.
Figure 4:
FIG. 4 schematically the final linear configuration of the catheter of the invention.

FIG. 1 schematically illustrates an embodiment of the invention, showing the catheter in its initial coiled configuration. In an embodiment the catheter of the invention is manufactured by winding a long narrow piece of biocompatible polymer (see FIG. 4) around a mandrel. The long narrow piece of polymer can be, for example, a thin ribbon, a cord, a string, or a small diameter tube made of, for example silicone rubber, nylon, polyurethane, or latex. The adjacent coils of material are weakly glued or welded together to maintain the catheter in its coiled configuration and also to provide a hermetic seal so that, when it is in its initial configuration, fluids can flow through the interior of the catheter after it is slid off the mandrel. In this embodiment, if the catheter is formed from a small-diameter tube, the interior of the small-diameter tube can also be used for various purposes, for example to transfer fluids, for example air or liquid to inflate an anchor balloon at the distal end of the catheter or to provide a conduit for passage of wires connected to a temperature sensor.

In another embodiment the catheter of the invention is manufactured by molding the biocompatible polymer into the shape of a tube having a wall comprising two parallel spirals, one having relatively thick and the other having relatively thin wall thickness.

In its initial configuration the catheter of the invention is similar to that of conventional catheters and can be used for any application in which a conventional catheter is used. The catheter of the invention formed by either method, i.e. winding or molding, can have all the same characteristics as a conventional prior-art catheter, including a balloon and a separate lumen for inflating it, an integral temperature sensor, coating its outer surface with antibacterial gel, looping a silver or copper wire around it to provide long-term antibacterial action, etc.

Figure 2:
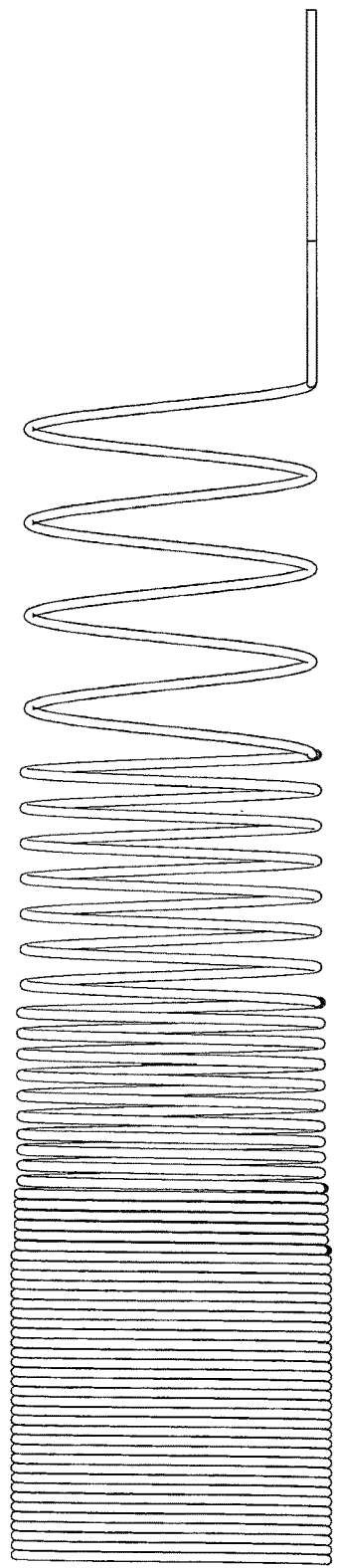
FIG. 2 and FIG. 3 schematically show two intermediate stages of the unraveling of the catheter of the invention.
Figure 3:
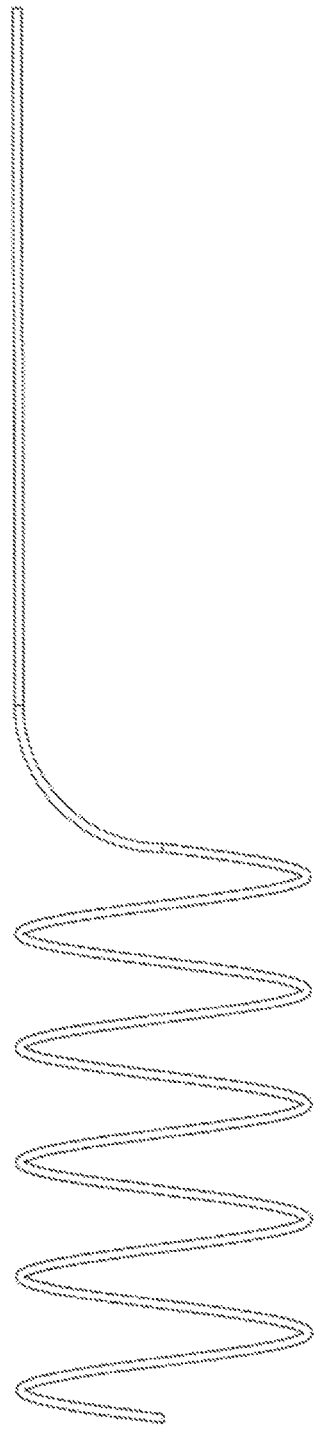

As the catheter 10 is pushed into a body lumen, e.g. the urethra, each loop is pushed against the loop that is distal to it, thereby maintaining the initial configuration of the catheter. When it is desired to remove catheter 10 from the lumen, the free proximal end of material 12 is pulled proximally by a nurse or doctor. Because of friction between the outer wall of the catheter and the inner wall of the lumen there will be a resistance to pulling the catheter out of the lumen and the force exerted by the person removing the catheter will be great enough to break the glue or weld bonds holding the coils of the catheter together and the catheter will begin to unravel. Two intermediate stages of the unraveling of the catheter are symbolically shown in FIG. 2 and FIG. 3 and the final linear configuration is symbolically shown in FIG. 4. As the catheter unravels from its proximal end, its diameter is reduced and it "falls away" from the wall of the lumen enabling the catheter to be removed with ease and causing minimal discomfort to the patient.

Embodiments of the invention that are manufactured by molding techniques will unravel in a similar manner, wherein the material tears along the spiral line of thinnest wall thickness when pulled in a proximal direction.

Embodiments of the catheter of the invention, whether formed by winding or molding, can be provided with a safety feature to prevent accidental unraveling of the catheter. The safety feature is provided by making the bond between at least parts of at least two of the coils that are in the proximal part of the catheter that extends outside of the body lumen stronger than the bonds between the other coils. This can be accomplished either inherently, e.g. by using a stronger glue or weld or molded thickness between the coils, or by adding an extra element such as a sticker that must be released before the catheter can be unraveled. When a safety feature is used, the initial unraveling may require an extra operation, such as removing the extra element or grasping the proximal end of the catheter with two hands to break the stronger bond.

In an embodiment of the invention, a catheter of the invention is inserted into the lumen of a thin walled conventional catheter. The catheter of the invention provides strength to allow the conventional catheter to be inserted into a body lumen of a patient and also expands the thin walled conventional catheter pushing it against the inner wall of the body lumen. When it is desired to remove the catheter from the body lumen the catheter of the invention is first removed from the conventional catheter by pulling proximally causing the catheter of the invention to unravel. When the internal support is removed, the conventional catheter collapses and can be easily withdrawn with minimal discomfort to the patient.

Although embodiments of the invention have been described by way of illustration, it will be understood that the invention may be carried out with many variations, modifications, and adaptations, without exceeding the scope of the claims.

The invention claimed is:

1. An unravelable catheter, having proximal and distal ends, which is formed from flexible material and has two basic configurations: an initial configuration, which has a shape resembling a tension coil spring, and a final configuration, which is essentially linear; said catheter adapted to undergo a transformation from said initial configuration to said final configuration as said catheter is pulled from the proximal end, wherein the unravelable catheter comprises a single, integral tube of molded polymer, said tube having a wall comprised of a first spiral and a second spiral, wherein said first spiral is parallel to the second spiral, and wherein the wall of the first spiral is thicker than the wall of the second spiral.

2. The unravelable catheter of claim 1, comprising at least one of the following: at least one balloon and a separate lumen for inflating the balloon, an integral temperature sensor, a coating of antibacterial gel on an outer surface of the catheter, a silver or copper wire looped around part or the outer surface in its entirety.

3. The unravelable catheter of claim 2, further comprising at least one balloon and a separate lumen coupled to and adapted to inflate the balloon.

4. The unravelable catheter of claim 2, further comprising an integral temperature sensor.

5. The unravelable catheter of claim 2, further comprising an antibacterial coating on the outer surface of the catheter.

6. The unravelable catheter of claim 2, further comprising a silver or copper wire looped around at least part of the outer surface of the catheter.

7. The unravelable catheter of claim 1, comprising at least one safety feature to prevent accidental unraveling of the catheter.

* * * * *